(12) United States Patent
Dos Santos et al.

(10) Patent No.: US 10,687,912 B2
(45) Date of Patent: Jun. 23, 2020

(54) FIBER-BASED MODE MIXING TECHNIQUES FOR SURGICAL LASER ILLUMINATION

(71) Applicant: Novartis AG, Basel (CH)

(72) Inventors: Cesario Dos Santos, Newport Beach, CA (US); Gerald David Bacher, Carlsbad, CA (US); Ronald Smith, Irvine, CA (US); Alireza Mirsepassi, Irvine, CA (US); Michael Papac, North Tustin, CA (US)

(73) Assignee: Alcon Inc., Fribourg (CH)

( * ) Notice: Subject to any disclaimer, the term of this patent is extended or adjusted under 35 U.S.C. 154(b) by 126 days.

(21) Appl. No.: 15/882,758

(22) Filed: Jan. 29, 2018

(65) Prior Publication Data

US 2018/0214237 A1 Aug. 2, 2018

Related U.S. Application Data

(60) Provisional application No. 62/453,744, filed on Feb. 2, 2017.

(51) Int. Cl.
| | |
|---|---|
| *A61B 90/30* | (2016.01) |
| *A61B 17/02* | (2006.01) |
| *A61F 9/007* | (2006.01) |
| *A61B 3/00* | (2006.01) |
| *G02B 27/09* | (2006.01) |
| *G02B 6/14* | (2006.01) |
| *A61B 18/22* | (2006.01) |

(52) U.S. Cl.
CPC ............ *A61B 90/30* (2016.02); *A61B 3/0008* (2013.01); *A61B 17/0231* (2013.01); *A61F 9/007* (2013.01); *A61F 9/00736* (2013.01); *G02B 6/14* (2013.01); *G02B 27/0994* (2013.01); *A61B 18/22* (2013.01); *A61B 2090/306* (2016.02)

(58) Field of Classification Search
CPC .............................. A61B 90/30; A61B 3/0008
See application file for complete search history.

(56) References Cited

U.S. PATENT DOCUMENTS

| | | | |
|---|---|---|---|
| 5,395,362 | A | 3/1995 | Sacharoff |
| 6,299,307 | B1 | 10/2001 | Oltean |
| 7,444,057 | B2 | 10/2008 | Dacquay |
| 7,499,624 | B2 | 3/2009 | Dacquay |
| 7,959,297 | B2 | 6/2011 | Silverstein |
| 8,944,647 | B2 | 2/2015 | Bueeler |

(Continued)

FOREIGN PATENT DOCUMENTS

| | | |
|---|---|---|
| CN | 103799961 A | 5/2014 |
| EP | 2945005 A1 * | 11/2015 |

(Continued)

OTHER PUBLICATIONS http://translationportal.epo.org/emtp/translate/?Action=claims-retrieval&COUNTRY=KR20110011052-Claims-en (Year: 2019).*

(Continued)

*Primary Examiner* — Christian A Sevilla

(57) ABSTRACT

Fiber-based mode mixing techniques may be used to homogenize different modes in an optical fiber used for surgical illumination. A vibrating fiber mechanism may impart mechanical motion to a portion of the optical fiber to generate a homogeneous illumination field from a coherent light source.

20 Claims, 5 Drawing Sheets

(56) References Cited

U.S. PATENT DOCUMENTS

| | | | |
|---|---|---|---|
| 10,238,543 B2 | 3/2019 | Farley | |
| 10,254,559 B2 | 4/2019 | Niederer | |
| 10,444,504 B2* | 10/2019 | Samec | A61B 3/12 |
| 2003/0229270 A1 | 12/2003 | Suzuki | |
| 2004/0151008 A1 | 8/2004 | Artsyukhovich | |
| 2005/0027288 A1* | 2/2005 | Oyagi | A61F 9/008 606/16 |
| 2005/0248849 A1 | 11/2005 | Urey | |
| 2006/0045501 A1 | 3/2006 | Liang | |
| 2007/0047059 A1 | 3/2007 | Howard | |
| 2008/0055698 A1 | 3/2008 | Yurlov | |
| 2008/0144148 A1 | 6/2008 | Kusunose | |
| 2008/0246919 A1 | 10/2008 | Smith | |
| 2008/0269731 A1 | 10/2008 | Swinger | |
| 2009/0059359 A1 | 3/2009 | Nahm et al. | |
| 2010/0157622 A1 | 6/2010 | Stocks | |
| 2011/0144745 A1 | 6/2011 | Martin | |
| 2012/0081786 A1 | 4/2012 | Mizuyama | |
| 2012/0176769 A1* | 7/2012 | Reimer | A61B 3/0008 362/84 |
| 2012/0203075 A1* | 8/2012 | Horvath | A61B 1/07 600/249 |
| 2013/0144278 A1 | 6/2013 | Papac | |
| 2013/0150839 A1 | 6/2013 | Smith | |
| 2013/0158392 A1 | 6/2013 | Papac | |
| 2013/0158393 A1 | 6/2013 | Papac | |
| 2013/0338648 A1 | 12/2013 | Hanebuchi | |
| 2014/0316417 A1* | 10/2014 | Kaiser | A61B 90/35 606/87 |
| 2014/0333978 A1 | 11/2014 | Hereen | |
| 2014/0350368 A1 | 11/2014 | Irisawa | |
| 2015/0277137 A1 | 10/2015 | Aschwanden | |
| 2015/0366443 A1 | 12/2015 | Liolios | |
| 2016/0338590 A1* | 11/2016 | Sagalovich | G16H 40/63 |
| 2018/0104009 A1* | 4/2018 | Abhari | A61B 1/00009 |
| 2018/0214018 A1 | 8/2018 | Dos Santos | |
| 2018/0214021 A1 | 8/2018 | Dos Santos | |
| 2018/0214237 A1 | 8/2018 | Dos Santos | |
| 2018/0214238 A1 | 8/2018 | Dos Santos | |
| 2018/0214239 A1 | 8/2018 | Dos Santos | |
| 2019/0125459 A1* | 5/2019 | Shelton, IV | A61B 34/25 |
| 2019/0201038 A1* | 7/2019 | Yates | A61B 5/068 |
| 2019/0314111 A1* | 10/2019 | Lassalas | A61F 9/008 |

FOREIGN PATENT DOCUMENTS

| | | | |
|---|---|---|---|
| EP | 3035110 A1 * | 6/2016 | |
| GB | 2467181 * | 7/2010 | |
| KR | 20110011052 * | 2/2011 | |
| KR | 20110011052 A | 2/2011 | |
| WO | 09314432 A2 | 7/1993 | |
| WO | WO-9314432 A2 * | 7/1993 | |
| WO | WO-2012122677 A1 * | 9/2012 | |
| WO | WO-2014053562 A1 * | 4/2014 | |
| WO | WO-2014059552 A1 * | 4/2014 | |

OTHER PUBLICATIONS https://web.archive.org/web/20160323050541/http://www.generalphotonics.com/index.php/product/pcd-m02-polarization-controller/ (Year: 2019).*

* cited by examiner

FIBER-BASED MODE MIXING TECHNIQUES FOR SURGICAL LASER ILLUMINATION

BACKGROUND

Field of the Disclosure

The present disclosure relates to surgical illumination, and more specifically, to fiber-based mode mixing techniques for surgical laser illumination.

Description of the Related Art

In ophthalmology, eye surgery, or ophthalmic surgery, is performed on the eye and accessory visual structures. More specifically, vitreoretinal surgery encompasses various delicate procedures involving internal portions of the eye, such as the vitreous humor and the retina. Different vitreoretinal surgical procedures are used, sometimes with lasers, to improve visual sensory performance in the treatment of many eye diseases, including epimacular membranes, diabetic retinopathy, vitreous hemorrhage, macular hole, detached retina, and complications of cataract surgery, among others.

During vitreoretinal surgery, an ophthalmologist typically uses a surgical microscope to view the fundus through the cornea, while surgical instruments that penetrate the sclera may be introduced to perform any of a variety of different procedures. The patient typically lies supine under the surgical microscope during vitreoretinal surgery and a speculum is used to keep the eye exposed. Depending on a type of optical system used, the ophthalmologist has a given field of view of the fundus, which may vary from a narrow field of view to a wide field of view that can extend to peripheral regions of the fundus.

Additionally, an illumination source is typically introduced into the fundus to illuminate the area where the surgeon will be working. The illumination source is typically implemented as a surgical tool having an illuminator assembly that also penetrates the sclera and may be combined with other surgical tools. The use of optical fibers transmitting coherent light as illumination sources for surgery is desirable because of the high light intensity provided within very small physical dimensions available with optical fibers.

SUMMARY

The disclosed embodiments of the present disclosure provide fiber-based mode mixing techniques used to homogenize different modes in an optical fiber used for surgical illumination. A vibrating fiber mechanism may impart mechanical motion to a portion of the optical fiber to generate a homogeneous illumination field from a coherent light source.

In one aspect, a disclosed method for surgical illumination includes projecting first light from a coherent light source into a first optical fiber, the coherent light source used for illumination of a patient during a surgery. The method may also include transmitting the first light from the first optical fiber to a fiber mode mixer device. In the method, the fiber mode mixer device may include an internal optical fiber receiving the first light and a vibrating fiber mechanism coupled to the internal optical fiber. In the method, the first light may be homogenized within the internal optical fiber by the vibrating fiber mechanism to generate second light output by the fiber mode mixer device. The method may further include transmitting the second light from the fiber mode mixer device to a second optical fiber. In the method, the second optical fiber may terminate in a third optical fiber that projects the second light onto the patient.

In any of the disclosed embodiments of the method, the surgery may be an ophthalmic surgery, while the third optical fiber may project the second light into an eye of the patient.

In any of the disclosed embodiments of the method, the coherent light source may be a monochromatic laser.

In any of the disclosed embodiments of the method, the coherent light source may be a plurality of monochromatic lasers combined to generate the first light.

In any of the disclosed embodiments of the method, the vibrating fiber mechanism may include a piezoelectric actuator mechanically coupled to the internal optical fiber.

In any of the disclosed embodiments of the method, the vibrating fiber mechanism may include an electromagnetic actuator mechanically coupled to the internal optical fiber.

In any of the disclosed embodiments of the method, the vibrating fiber mechanism may include a mechatronic actuator mechanically coupled to the internal optical fiber.

In any of the disclosed embodiments of the method, the vibrating fiber mechanism may impart at least one of a reciprocal motion and a circular motion to at least a portion of the internal optical fiber.

In any of the disclosed embodiments of the method, the vibrating fiber mechanism may impart a randomized motion to at least a portion of the internal optical fiber.

In any of the disclosed embodiments of the method, the fiber mode mixer device may further include an input optical connector for connection to the first optical fiber, an output optical connector for connection to the second optical fiber, and a power source to power the vibrating fiber mechanism. In the method, the vibrating fiber mechanism may cause the internal optical fiber to reciprocate at a frequency greater than 30 Hz.

In another aspect, a disclosed optical fiber homogenizer device is for surgical illumination. The optical fiber homogenizer device may include an input optical connector for connection to a first optical fiber transmitting first light from a coherent light source used for illumination of a patient during a surgery, an internal optical fiber coupled to the input connector to receive the first light. The optical fiber homogenizer device may also include a vibrating fiber mechanism mechanically coupled to the internal optical fiber. In the optical fiber homogenizer device, the first light may be homogenized within the internal optical fiber by the vibrating fiber mechanism to generate second light output by the optical fiber homogenizer device. The optical fiber homogenizer device may further include an output optical connector for connection to a second optical fiber, the output optical connector receiving the second light from the internal optical fiber. In the optical fiber homogenizer device, the second optical fiber may terminate in a third optical fiber that projects the second light onto the patient.

In any of the disclosed embodiments of the optical fiber homogenizer device, the surgery may be an ophthalmic surgery, and the third optical fiber may project the second light into an eye of the patient.

In any of the disclosed embodiments of the optical fiber homogenizer device, the coherent light source may be a monochromatic laser.

In any of the disclosed embodiments of the optical fiber homogenizer device, the coherent light source may be a plurality of monochromatic lasers combined to generate the first light.

In any of the disclosed embodiments of the optical fiber homogenizer device, the vibrating fiber mechanism may include a piezoelectric actuator mechanically coupled to the internal optical fiber.

In any of the disclosed embodiments of the optical fiber homogenizer device, the vibrating fiber mechanism may include an electromagnetic actuator mechanically coupled to the internal optical fiber.

In any of the disclosed embodiments of the optical fiber homogenizer device, the vibrating fiber mechanism may include a mechatronic actuator mechanically coupled to the internal optical fiber.

In any of the disclosed embodiments of the optical fiber homogenizer device, the vibrating fiber mechanism may impart at least one of a reciprocal motion and a circular motion to at least a portion of the internal optical fiber.

In any of the disclosed embodiments of the optical fiber homogenizer device, the vibrating fiber mechanism may impart a randomized motion to at least a portion of the internal optical fiber.

In any of the disclosed embodiments of the optical fiber homogenizer device, the vibration fiber mechanism may cause the internal optical fiber to reciprocate at a frequency greater than 30 Hz.

BRIEF DESCRIPTION OF THE DRAWINGS

For a more complete understanding of the present disclosure and its features and advantages, reference is now made to the following description, taken in conjunction with the accompanying drawings, in which.

DESCRIPTION

Figure 1:
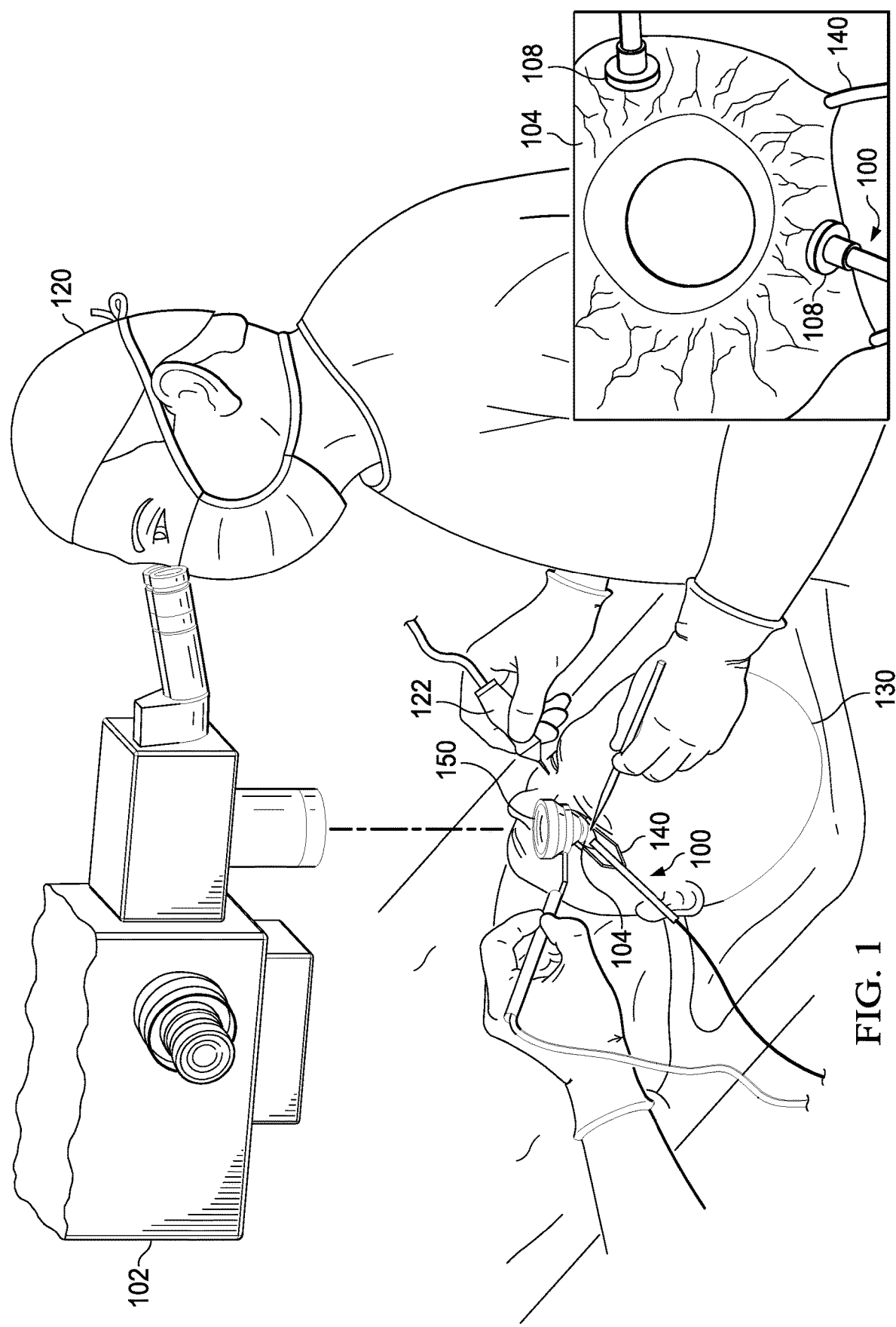
FIG. 1 is a depiction of an embodiment of an ophthalmic surgery using a surgical microscope and a surgical tool with an illuminator assembly.

In the following description, details are set forth by way of example to facilitate discussion of the disclosed subject matter. It should be apparent to a person of ordinary skill in the field, however, that the disclosed embodiments are exemplary and not exhaustive of all possible embodiments.

As used herein, a hyphenated form of a reference numeral refers to a specific instance of an element and the un-hyphenated form of the reference numeral refers to the collective element. Thus, for example, device '12-1' refers to an instance of a device class, which may be referred to collectively as devices '12' and any one of which may be referred to generically as a device '12'.

As noted above, the use of optical fibers and coherent light sources is desirable for surgical illumination because of the high light intensity provided within the very small physical dimensions of an optical fiber. Although such surgical illumination sources may be used in various medical and surgical applications, one exemplary application is in eye surgery, such as for vitreoretinal surgery.

For vitreoretinal surgery, for example, the illumination source is typically implemented as a surgical tool having an illuminator assembly that penetrates the sclera and may be combined with other surgical tools. At a distal end of the illuminator assembly, a very small diameter optical fiber may be used to project light into the fundus to illuminate surgical procedures performed within the eye. The very small diameter fiber, for example having a fiber core of about 25-100 μm, is typically coupled to an optical fiber that couples proximally to a coherent light source, such as a laser source. Although various types of optical fibers may be used, multi-mode optical fibers may be used to transmit coherent light into the eye for illumination.

However, as coherent light is transmitted through a multi-mode optical fiber, different groups of photons of the coherent light, referred to as "modes", within the fiber may traverse slightly different path lengths. As a result of the different path lengths experienced by different modes within the optical fiber, the modes may constructively and destructively interfere with each other during propagation within the optical fiber. As the different modes exit the optical fiber from a fiber core, an illumination field provided by the exiting light may appear inhomogeneous due to the inter-mode interference. The inter-mode interference may be highly sensitive to temperature, fiber strain, fiber motion, and may generally become quite noticeable to the human eye, since the inhomogeneous illumination field projects an undesired dynamic pattern, instead of a homogeneous illumination field projecting uniform background light. Because the inhomogeneous illumination field appears as different regions of different colored light that may be dynamic, the inhomogeneous illumination field may be poorly suited for surgical illumination.

For example, in vitreoretinal surgery, a clear and unambiguous view of various fine biostructures in the eye is highly desirable to enable a surgeon to operate safely and effectively, which the inhomogeneous illumination field may not provide. In particular, the inhomogeneous illumination field is observed with monochromatic laser sources, or combinations of monochromatic laser sources in some implementations. The monochromatic laser sources may exhibit fewer modes and, thus, a lesser degree of mode mixing within the optical fiber that enables homogenization of the coherent light into a desired homogeneous illumination field. Furthermore, as various surgical tools are designed and implemented, such as endoilluminators or surgical tools with combined illumination, the use of smaller fiber diameters carrying high light intensity becomes increasingly desirable. However, the inter-mode interference issues become increasingly exacerbated as the size (i.e., diameter) of an optical fiber decreases, which may undesirably constrain the use of such compact illumination systems. Also, in surgical illumination applications, a relatively short length of optical fiber is used, such as about 2-3 m in length. Because mode mixing that leads to a more homogeneous illumination field increases with fiber length, shorter optical fibers used in in surgical illumination applications may experience insufficient mode mixing that results in the inhomogeneous illumination field. Also, optical fibers comprised of a glass core may exhibit fewer modes and less mode mixing, and may be particularly subject to the inhomogeneous illumination field.

As will be described in further detail, fiber-based mode mixing techniques for surgical laser illumination are disclosed. The fiber-based mode mixing techniques for surgical laser illumination disclosed herein may provide a homogeneous illumination field for surgical illumination using optical fibers to transmit coherent light. The fiber-based mode mixing techniques for surgical laser illumination disclosed herein may be used with relatively short and relatively small diameter optical fibers. The fiber-based mode mixing techniques for surgical laser illumination disclosed herein may be used with optical fibers having a glass core. The fiber-based mode mixing techniques for surgical laser illumination disclosed herein may be implemented at a light source for surgical illumination. The fiber-based mode mixing techniques for surgical laser illumination disclosed herein may be implemented as an optical device that can be coupled to an optical fiber providing surgical illumination from a coherent light source. The fiber-based mode mixing techniques for surgical laser illumination disclosed herein may be used for illumination of a patient's eye during ophthalmic surgery, such as vitreoretinal surgery.

One manner in which an illumination assembly 100 may be used is illustrated in FIG. 1, in which a surgeon 120 is performing an ophthalmic surgery on an eye 104 of a patient 130 using a surgical tool 122. In FIG. 1, the eye 104 has been exposed using a speculum 140 and a contact lens 150 is held in place on the eye 104 and visually aligned with a surgical microscope 102 to facilitate visualization of inner structures of the eye 104. The surgeon 120 is using the surgical tool 122 to perform surgery on inner structures of the eye 104.

For example, when the surgical tool 122 is a vitrectomy probe, then the surgeon 120 may be using the surgical tool 122 to remove the clear, gel-like vitreous that normally fills the interior of the eye 104, taking care to remove substantially only the vitreous, while avoiding interaction with nearby eye structures, such as the retina, that are extremely sensitive to any mechanical action. The ability of the surgeon to clearly view the fundus is facilitated by a homogenous illumination field that is provided by illumination assembly 100. It is noted that surgical tool 122 may by any of a variety of handheld surgical tools. In some embodiments, illumination assembly 100 may be integrated within surgical tool 122 to provide illumination without having to use a secondary illumination tool.

In the inset of FIG. 1, additional details of the eye 104 during surgery are shown. Two scleral ports 108 for providing cannulated scleral penetration are visible, one for surgical tool 122 and one for illuminator assembly 100. As shown, illuminator assembly 100 may include a means for fiber-based mode mixing for surgical laser illumination, as described in further detail below. Accordingly, illuminator assembly 100 may be used to project coherent light into the eye 104 using an optical fiber to transmit the light to project a homogenous illumination field (not visible in FIG. 1) into the fundus.

Modifications, additions, or omissions may be made to illuminator assembly 100 without departing from the scope of the disclosure. The components and elements of surgical illuminator assembly 100, as described herein, may be integrated or separated according to particular applications. Illuminator assembly 100 may be implemented using more, fewer, or different components in some embodiments.

Figure 2:
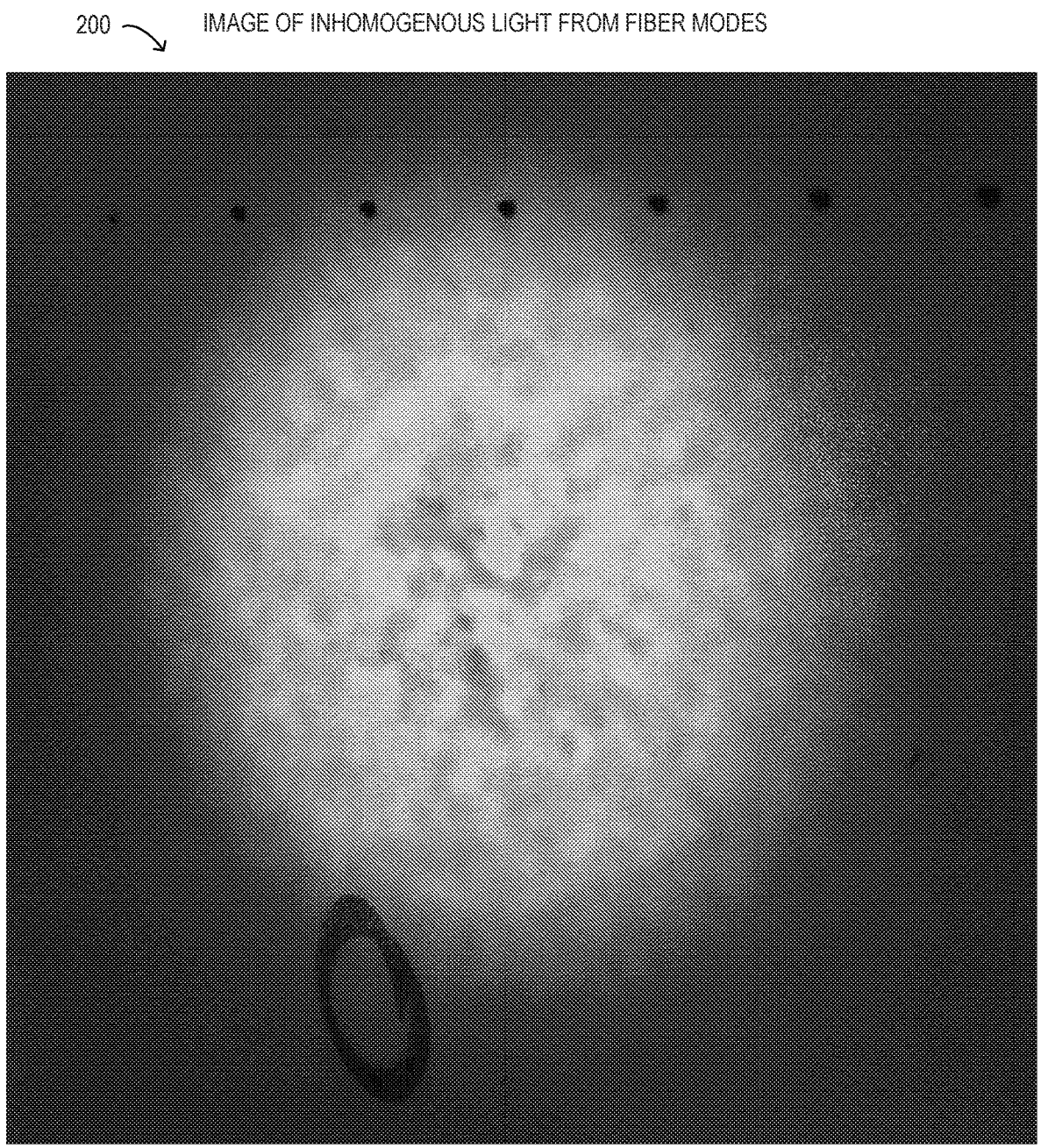
FIG. 2 is an image of inhomogeneous light from fiber modes.

FIG. 2 illustrates an image 200 of inhomogeneous light from fiber modes. Image 200 depicts coherent light from an optical fiber projected onto a screen that is oriented oblique to the page. In image 200, the depicted screen has extraneous annotations written in black ink above and below the inhomogeneous illumination field. The inhomogeneous illumination field in image 200 results from insufficient mode mixing within the optical fiber. The inhomogeneous illumination field in image 200 may exhibit intensity variations up to about 500%, which may be dynamic in many applications and usage scenarios, which is undesirable for surgical illumination, as explained previously. The inhomogeneous illumination field in image 200 may be immediately converted into a homogeneous illumination field, such as a substantially uniform intensity illumination field (not shown) by applying the techniques for mode mixing disclosed herein.

Figure 3:
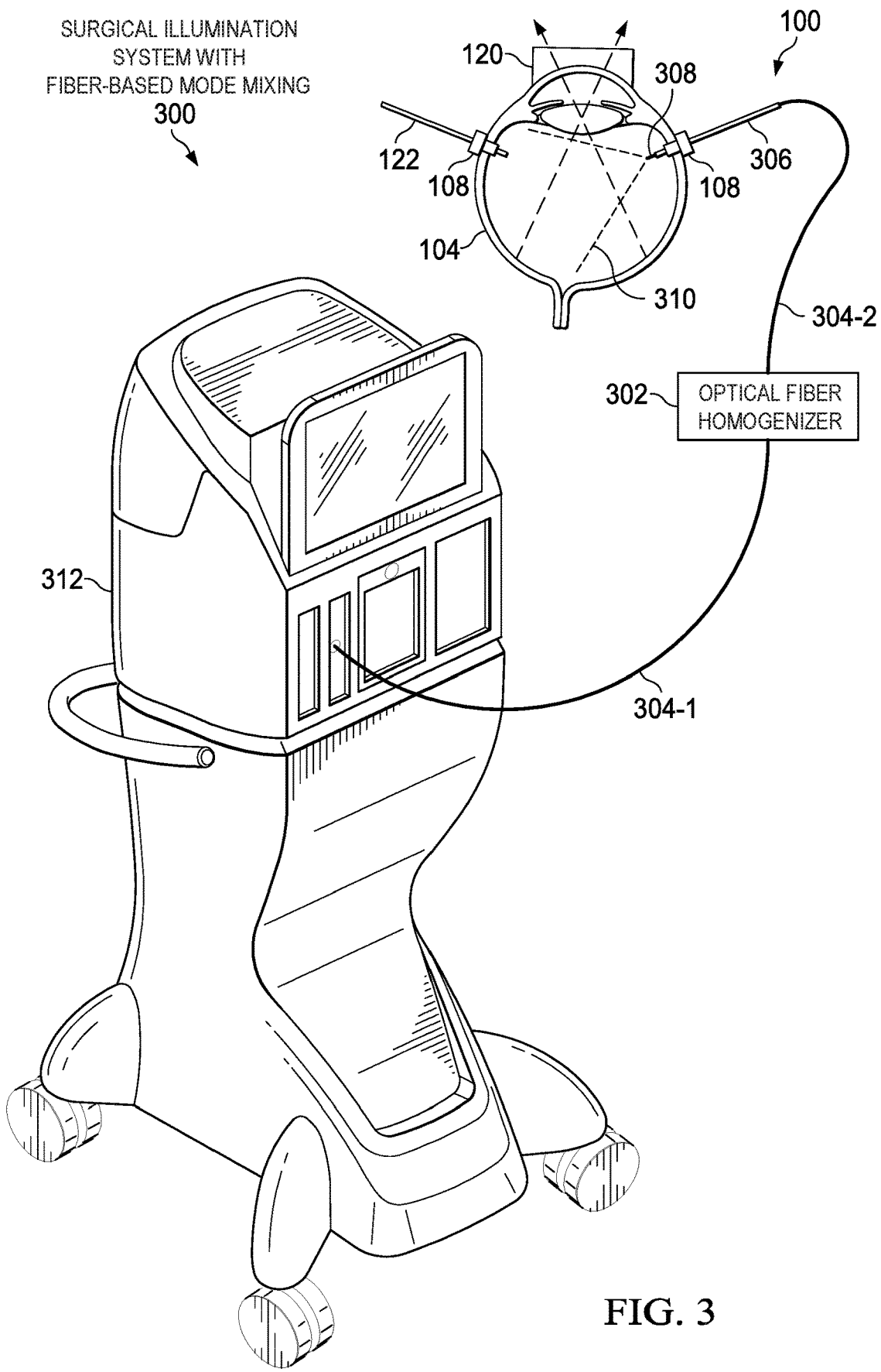
FIG. 3 is a depiction of an embodiment of a surgical illumination system with fiber-based mode mixing.

Referring now to FIG. 3, a depiction of an embodiment of a surgical illumination system 300 is shown. As shown in FIG. 3, surgical illumination system 300 may be used in the ophthalmic surgery on the eye 104 shown in FIG. 1. FIG. 3 is a schematic illustration and is not drawn to scale or perspective. In FIG. 3, a cross-sectional view of the eye 104 is shown, enabling a view of various elements described above with respect to FIG. 1. Specifically, contact lens 120 is shown providing a relatively wide angle view of the fundus of the eye 104, while two scleral ports 108 penetrate the sclera of the eye 104. A surgical tool 122 is shown penetrating one scleral port 108, while illumination assembly penetrates another scleral port 108.

As shown in FIG. 3, a homogeneous illumination field 310 is projected into the eye 104 by illuminator assembly 100. Specifically, illuminator assembly 100 terminates distally with an optical fiber portion 308, which may be exposed to project light into the eye. Optical fiber portion 308 is coupled to an external optical fiber 304. In some embodiments, optical fiber portion 308 may be a distal portion of external optical fiber 304 itself. Optical fiber 304 is shown having a first section of optical fiber 304-1 that extends from a surgical console 312 to an optical fiber homogenizer 302, and a second section of optical fiber 304-2 that extends from optical fiber homogenizer 302 to optical fiber 308. Also, second section of optical fiber 304-2 is shown passing through a hand piece 306, which may include a sheath or tube around optical fiber 304-2 to enable cannulation at scleral port 108.

In FIG. 3, optical fiber homogenizer 302 may apply fiber-based mode mixing techniques for surgical laser illumination, as disclosed herein. Specifically, optical fiber homogenizer 302 may apply mechanical movement or vibration to an optical fiber (not visible in FIG. 3) in order to perform mode mixing and to homogenize the second light transmitted by optical fiber 304-2. In this manner, optical fiber homogenizer 302 provides homogeneous illumination field 310 in the eye 104 during surgery. Optical fiber homogenizer 302 may include optical connectors for connection to optical fibers 304-1 and 304-2, respectively. In some embodiments, optical fiber homogenizer 302 may be implemented within or integrated with surgical console 312, which may also include a coherent light source (not visible) to generate homogeneous illumination field 310. Surgical console 312 may provide various other equipment and functionality, such as driver equipment for surgical tool 122, and a user interface for data operations and image processing. Further internal details of optical fiber homogenizer 302 are described below with respect to FIG. 4.

Figure 4:
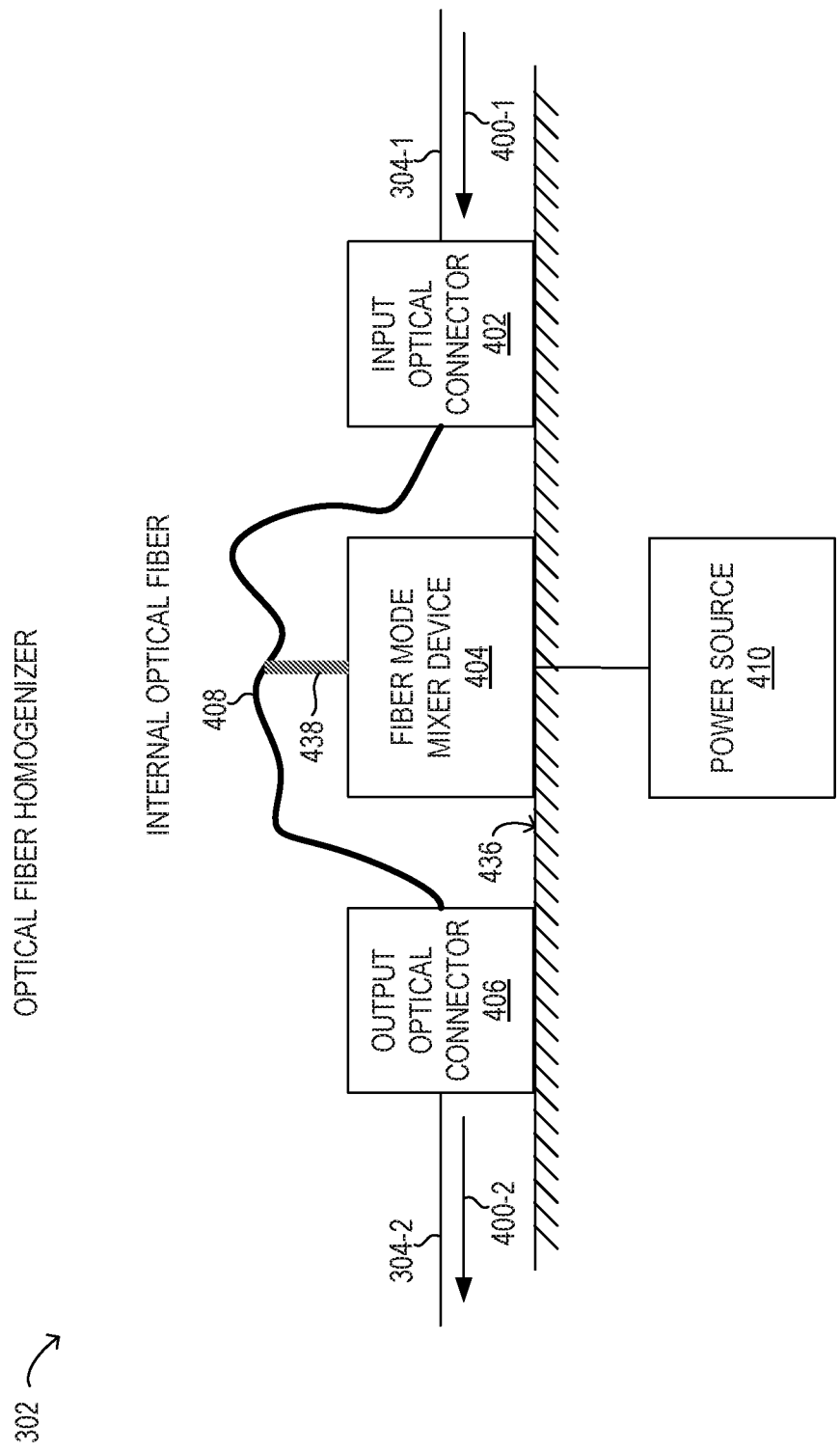
FIG. 4 is a depiction of an embodiment of an optical fiber homogenizer.

Referring now to FIG. 4, further details of optical fiber homogenizer 302 are depicted. FIG. 4 is a schematic illustration and is not drawn to scale or perspective. In FIG. 4, elements included within optical fiber homogenizer 302 are shown schematically. It will be understood that optical fiber homogenizer 302 may be implemented as an optical device, for example having an enclosure (not shown) to house the components illustrated in FIG. 4.

Specifically, optical fiber homogenizer 302 is shown having input optical connector 402 for connecting to optical fiber 304-1, as well as having output optical connector 406 for connecting to optical fiber 304-2. In various embodiments, input optical connector 402 and output optical connector 406 may be releasable connectors (not shown) that mate with corresponding connectors attached to optical fibers 304-1 and 304-2. In some embodiments, input optical connector 402 and output optical connector 406 may be fixed connectors. As shown, input optical connector 402, output optical connector 406, and a fiber mode mixer device 404 are situated on a fixed surface 436, which may represent a base of a housing (not shown) which may enclose optical fiber homogenizer 302. Input optical connector 402 may receive first light 400-1, which may experience insufficient mode mixing in optical fiber 304-1 after being transmitted from a coherent light source (not shown). The coherent light source may be a monochromatic laser, or a combination of monochromatic lasers that have been combined to generate first light 400-1. Accordingly, first light 400-1 may include light from different frequencies (i.e., colors).

Also shown in FIG. 4 with optical fiber homogenizer 302 is internal optical fiber 408, which is coupled to fiber mode mixer device 404 by an attachment 438. A length of internal optical fiber 408 may vary and may be adjusted according to desired physical dimensions of optical fiber homogenizer 302. Attachment 438 may represent any type of mechanical attachment or fixture or member to couple to internal optical fiber 408. For example, attachment 438 may include a clamp to attach externally to a portion of internal optical fiber 408. Fiber mode mixer device 404 may include a vibrating fiber mechanism comprised of mechanical components for moving or vibrating attachment 438, to which fiber mode mixer device 404 is fixed. The vibrating fiber mechanism may include any of a variety of mechanical actuators for generating motion of attachment 438, and thereby imparting motion to internal optical fiber 408, which is not otherwise connected to fixed surface 436. Examples of mechanical components or actuators included in fiber mode mixer device 404 may encompass rotating motors, linear motors, piezoelectric actuators, pneumatic actuators, hydraulic actuators, electromagnetic actuators, and mechatronic actuators, among various different combinations. The vibrating fiber mechanism may enable vibration, rotation, translation, or a combination thereof. Accordingly, the vibrating fiber mechanism may impart at least one of a reciprocal motion and a circular motion to at least a portion of internal optical fiber 408. In some embodiments, the vibrating fiber mechanism may impart a randomized motion to internal optical fiber 408. Electromagnetic actuators may include various actuators with magnets or magnet windings (electromagnets) that are electronically controlled. Mechatronic actuators may include various combinations of electronic and mechanical systems or components, such as integrated robotic drives.

Because fiber mode mixer device 404 is coupled externally to internal optical fiber 408, a high degree of precision in the motion imparted to internal optical fiber 408 may be superfluous, and a lesser degree of precision may be suitable for the desired mode mixing effect to homogenize second light 400-2 that exits internal optical fiber 408 to optical fiber 304-2 via output optical connector 406. In different embodiments, fiber mode mixer device 404 may reciprocate, rotate, or oscillate at a frequency to cause motion that is not visible to the human eye, such as at a frequency of about 30 Hz or greater. In this manner, fiber mode mixer device 404 may cause mode mixing within internal optical fiber 408 to generate homogeneous illumination field 310 that appears uniform to the human eye.

Also shown with optical fiber homogenizer 302 in FIG. 4 is power source 410, which may provide power to the mechanical components included with fiber mode mixer device 404. In some embodiments, power source 410 may represent an internal power source to optical fiber homogenizer 302, such as a battery to enable remote operation. In other embodiments, power source 410 may represent an external power source, such as a connector for line power or direct current from an external power supply (not shown).

Figure 5:
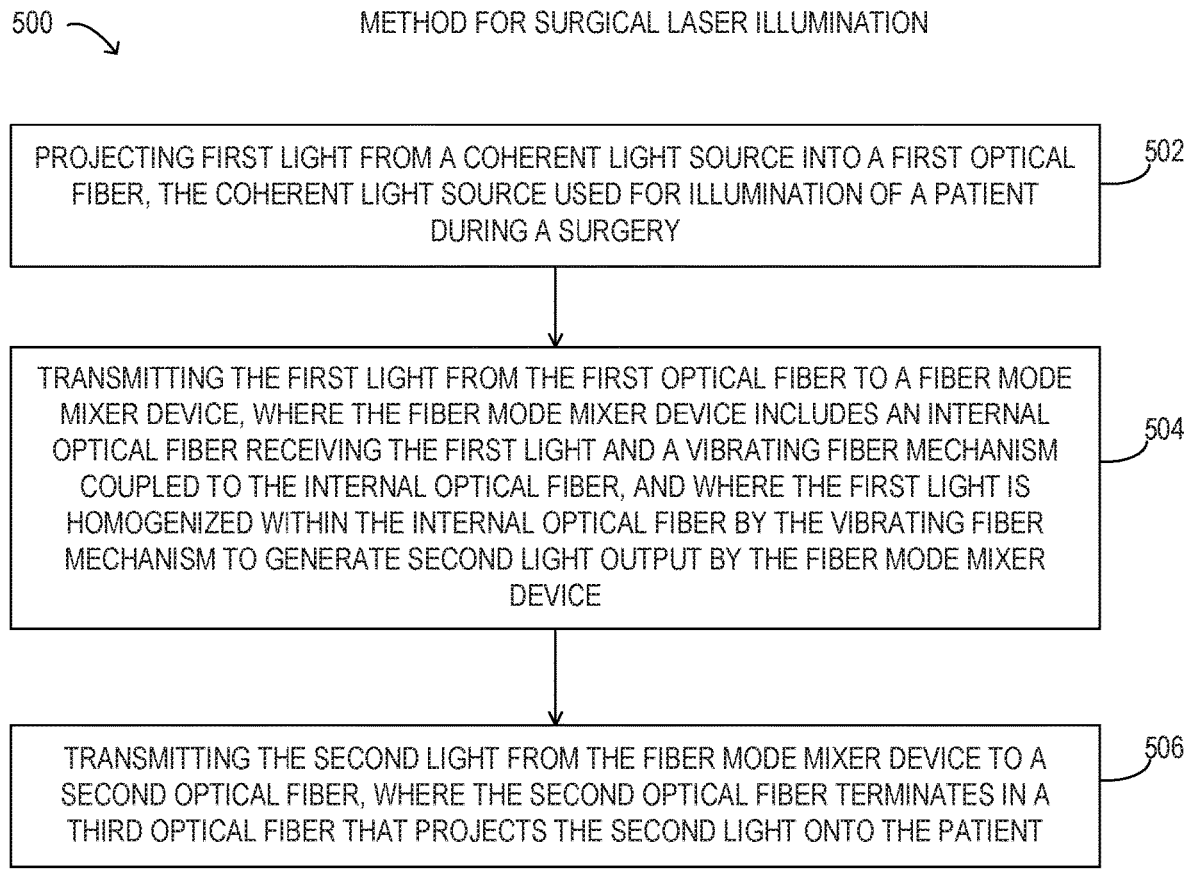
FIG. 5 is a flow chart of selected elements of a method for surgical laser illumination.

Referring now to FIG. 5, a flow chart of selected elements of an embodiment of a method 500 for fiber-based mode mixing techniques for surgical laser illumination, as described herein, is depicted in flowchart form. It is noted that certain operations described in method 500 may be optional or may be rearranged in different embodiments. Method 500 may be performed using illumination assembly 100 and optical fiber homogenizer 302, as described herein.

Method 500 may begin, at step 502, by projecting first light from a coherent light source into a first optical fiber, the coherent light source used for illumination of a patient during a surgery. At step 504, the first light is transmitted from the first optical fiber to a fiber mode mixer device, where the fiber mode mixer device includes an internal optical fiber receiving the first light and a vibrating fiber mechanism coupled to the internal optical fiber, and where the first light is homogenized within the internal optical fiber by the vibrating fiber mechanism to generate second light output by the fiber mode mixer device. At step 506, the second light is transmitted from the fiber mode mixer device to a second optical fiber, where the second optical fiber terminates in a third optical fiber that projects the second light onto the patient.

As disclosed herein, fiber-based mode mixing techniques may be used to homogenize different modes in an optical fiber used for surgical illumination. A vibrating fiber mechanism may impart mechanical motion to a portion of the optical fiber to generate a homogeneous illumination field from a coherent light source.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A method for surgical illumination, the method comprising:
   projecting first light from a coherent light source into a first optical fiber, the coherent light source used for illumination of a patient during a surgery;
   transmitting the first light from the first optical fiber to a fiber mode mixer device, wherein the fiber mode mixer device includes an internal optical fiber receiving the first light and a vibrating fiber mechanism coupled to the internal optical fiber, wherein the first light is homogenized within the internal optical fiber by the vibrating fiber mechanism to generate second light output by the fiber mode mixer device; and
   transmitting the second light output from the fiber mode mixer device to a second optical fiber.

2. The method of claim 1,
   wherein the second optical fiber terminates in a third optical fiber that projects the second light output onto the patient;

wherein the surgery is an ophthalmic surgery, and the third optical fiber projects the second light output into an eye of the patient.

3. The method of claim 1, wherein the coherent light source is a monochromatic laser.

4. The method of claim 1, wherein the coherent light source is a plurality of monochromatic lasers combined to generate the first light.

5. The method of claim 1, wherein the vibrating fiber mechanism includes a piezoelectric actuator mechanically coupled to the internal optical fiber.

6. The method of claim 1, wherein the vibrating fiber mechanism includes an electromagnetic actuator mechanically coupled to the internal optical fiber.

7. The method of claim 1, wherein the vibrating fiber mechanism includes a mechatronic actuator mechanically coupled to the internal optical fiber.

8. The method of claim 1, wherein the vibrating fiber mechanism imparts at least one of a reciprocal motion and a circular motion to at least a portion of the internal optical fiber.

9. The method of claim 1, wherein the vibrating fiber mechanism imparts a randomized motion to at least a portion of the internal optical fiber.

10. The method of claim 1, wherein the fiber mode mixer device further comprises:
an input optical connector for connection to the first optical fiber;
an output optical connector for connection to the second optical fiber; and
a power source to power the vibrating fiber mechanism, wherein the vibrating fiber mechanism causes the internal optical fiber to reciprocate at a frequency greater than 30 Hz.

11. A optical fiber homogenizer device for surgical illumination, the optical fiber homogenizer device comprising:
an input optical connector for connection to a first optical fiber transmitting first light from a coherent light source used for illumination of a patient during a surgery;
an internal optical fiber coupled to the input connector to receive the first light;
a vibrating fiber mechanism mechanically coupled to the internal optical fiber, wherein the first light is homogenized within the internal optical fiber by the vibrating fiber mechanism to generate second light output by the optical fiber homogenizer device; and
an output optical connector for connection to a second optical fiber, the output optical connector receiving the second light output from the internal optical fiber.

12. The optical fiber homogenizer device of claim 11, wherein the second optical fiber terminates in a third optical fiber that projects the second light output onto the patient;
wherein the surgery is an ophthalmic surgery, and the third optical fiber projects the second light output into an eye of the patient.

13. The optical fiber homogenizer device of claim 11, wherein the coherent light source is a monochromatic laser.

14. The optical fiber homogenizer device of claim 11, wherein the coherent light source is a plurality of monochromatic lasers combined to generate the first light.

15. The optical fiber homogenizer device of claim 11, wherein the vibrating fiber mechanism includes a piezoelectric actuator mechanically coupled to the internal optical fiber.

16. The optical fiber homogenizer device of claim 11, wherein the vibrating fiber mechanism includes an electromagnetic actuator mechanically coupled to the internal optical fiber.

17. The optical fiber homogenizer device of claim 11, wherein the vibrating fiber mechanism includes a mechatronic actuator mechanically coupled to the internal optical fiber.

18. The optical fiber homogenizer device of claim 11, wherein the vibrating fiber mechanism imparts at least one of a reciprocal motion and a circular motion to at least a portion of the internal optical fiber.

19. The optical fiber homogenizer device of claim 11, wherein the vibrating fiber mechanism imparts a randomized motion to at least a portion of the internal optical fiber.

20. The optical fiber homogenizer device of claim 11, wherein the vibration fiber mechanism causes the internal optical fiber to reciprocate at a frequency greater than 30 Hz.

* * * * *